United States Patent [19]

Takada et al.

[11] Patent Number: 5,677,305

[45] Date of Patent: Oct. 14, 1997

[54] OXOPYRIDINYLQUINOXALINE DERIVATIVE

[75] Inventors: Susumu Takada, Kawanishi; Nobuo Chomei, Sakai; Makoto Adachi, Nara-ken; Masami Eigyo, Ikoma; Kazuo Kawasaki, Nara, all of Japan

[73] Assignee: Shionogi & Co., Ltd., Osaka, Japan

[21] Appl. No.: 418,196

[22] Filed: Apr. 7, 1995

[30] Foreign Application Priority Data

Apr. 8, 1994 [JP] Japan ................................ 6-070909

[51] Int. Cl.⁶ .................. C07D 241/36; C07D 241/38; A01N 43/60
[52] U.S. Cl. ................. 514/249; 544/353; 544/356; 544/355
[58] Field of Search ...................... 514/250, 249; 541/353, 355, 356

[56] References Cited

FOREIGN PATENT DOCUMENTS

| A 0 511 152 | 10/1992 | European Pat. Off. . |
|---|---|---|
| A 0 572 852 | 12/1993 | European Pat. Off. . |
| 63-83074 | 4/1988 | Japan . |
| 63-258466 | 10/1988 | Japan . |
| 1-153680 | 6/1989 | Japan . |
| 2-48578 | 2/1990 | Japan . |
| 2-221263 | 9/1990 | Japan . |
| 2-221264 | 9/1990 | Japan . |
| WO 92/07847 | 5/1992 | WIPO . |

OTHER PUBLICATIONS

P. Birch et al., "6,7-Dinitro-quinoxaline-2,3-dion and 6-Nitro,7-cyano-quinoxaline-2,3-dion Antagonise Responses to NMDA in the Rat Spinal Cord via an Action at the Strychnine-Insensitive Glycine Receptor", *Eur. J. Pharmacol.*, 156, pp. 177–180 (1988).

J. Drejer et al., "Glycine Reverses the Effect of HA-966 on NMDA Responses in Cultured Rat Cortical Neurons and in Chick Retina", *Neurosci. Lett.*, 98, pp. 333–338 (1989).

E. Fletcher & D. Lodge, "Glycine Reverses Antagonism of N-Methyl-D-aspartate (NMDA) by 1-Hydroxy-3-aminopyrrolidone-2 *HA-966) but not by D-2-Amino-5-phophonovalerate (D-AP5) on Rat Cortical Slices", *Eur. J. Pharmacol.*, 151, pp. 161–162 (1988).

T. Honoré et al., "Quinoxalinediones: Potent Competitive Non-NMDA Glutamate Receptor Antagonists", *Science*, 241, pp. 701–703 (1988).

P. Jacobsen et al., "Quinoxalinediones as AMPA Receptor Antagonists: Mechanism and Structure–Activity Studies", *Excitatory Amino Acid Receptors: Design of Agonists and Antagonists*, pp. 246–259 (P. Krogsgaard-Larsen & J. Hansen eds., 1992).

J. Mosinger et al., "Blockade of Both NMDA and Non–NMDA Receptors Is Required for Optimal Protection Against Ischemic Neuronal Degeneration in the in Vivo Adult Mammalian Retina", *Exp. Neurol.*, 113, pp. 10–17 (1991).

M. Sheardown et al., "A Potent Antagonist of the Strychnine Insensitive Glycine Receptor Has Anticonvulsant Properties", *Eur. J. Pharmacol.*, 174, pp. 197–204 (1989).

M. Sheardown et al., "2,3-Dihydroxy-6-nitro-7-sulfamoyl-benzo(F)quinoxaline: A Neuroprotectant for Cerebral Ischemia", *Science*, 247, pp. 571–574 (1990).

*Primary Examiner*—Jeffrey C. Mullis
*Attorney, Agent, or Firm*—Fish & Neave; James F. Haley, Jr.

[57] ABSTRACT

An oxopyridinylquinoxaline derivative represented by the following Formula I or pharmaceutically acceptable salts thereof:

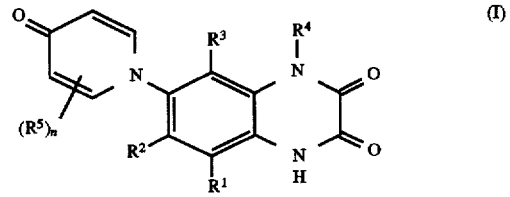

(I)

wherein $R^1$ is hydrogen, halogen, nitro, or trihalomethyl; $R^2$ is hydrogen, halogen, nitro, cyano, trihalomethyl, carbamoyl, carbamoyl substituted with lower alkyl, sulfamoyl, or sulfamoyl substituted with lower alkyl; $R^3$ is hydrogen, nitro, or halogen; $R^4$ is hydrogen, lower alkyl, substituted lower alkyl, lower cycloalkyl, or substituted lower cycloalkyl; $R^5$'s are substituents independently selected from the group consisting of halogen, nitro, cyano, lower alkyl, carbamoyl, and carbamoyl substituted with lower alkyl; and n is an integer of 0 to 4. The derivative works as an antagonistic agent against both the NMDA receptors and the AMPA receptors, so that it is effective as a therapeutic agent for neurological disorders caused by excitatory amino acids binding to the receptors.

10 Claims, No Drawings

OXOPYRIDINYLQUINOXALINE DERIVATIVE

BACKGROUND OF THE INVENTION

1. Field of the Invention

The present invention relates to an oxopyridinylquinoxaline derivative exhibiting antagonistic effects against glutamate receptors of central neurons, in particular, NMDA receptors and AMPA receptors.

2. Description of the Related Art

Amino acids such as L-glutamic acid and L-aspartic acid are indispensable as neurotransmitters for activating neurons in the central nervous system (CNS). However, excess accumulation of these excitatory amino acids surrounding neurons is considered to induce hyperstimulation of neurons, causing neurological disorders such as Parkinsonism, senile dementia, Huntington's disease, and epilepsy; and hyponoia and hypokinesis found after ischemia, anoxia, hypoglycemia, or head and spinal cord trauma (see, McGeer et al. Nature, 263, 517–519 (1976); Simon et al. Science, 226, 850–852 (1984), Wieloch, Science, 230, 681–683 (1985); Faden et al. Science, 244, 798–800 (1989); Turski et al. Nature, 349, 414–418 (1991)).

It has been known that the above-mentioned excitatory amino acids act on the CNS via a glutamate receptor on the neurons. Thus, compounds for competitively inhibiting the binding of the excitatory amino acids to such a receptor have been considered to be effective as therapeutic agents for the above-mentioned diseases and conditions, such as antiepileptic, ischemic encephalopathy preventive, and antiparkinsonism agent. Important roles performed by the glutamate receptor are reported by Japanese Laid-Open Patent Publication Nos. 6-25294, 6-239747, and 6-228112 (Yamanouchi Pharmaceutical Co., Ltd.); WO93/8173 (SCHERING); EP5725852A1 (BASF); etc.

The glutamate receptor can be classified into two groups; namely an ion channel type and a metabolism type. The ion channel type is further classified into three groups based on its selectivity with respect to binding to an agonist. These are called N-methyl-D-aspartate (NMDA) receptors, 2-amino-3-(3-hydroxy-5-methylisoxazol-4-yl)propanoate (AMPA) receptors, and kainate receptors.

The NMDA receptors are selectively activated by agonists such as NMDA and ibotenic acid. Hyper-stimulation of the NMDA receptors allows a large amount of calcium ions to flow into neurons, which has been considered one of the causes for the death of neurons. Hithertofore, as antagonists selectively binding to the NMDA receptors, D-2-amino-5-phosphovalerate (D-AP5), and 3-[2-carboxypiperazin-4-yl] propyl-1-phosphate(CPP), etc. are known.

The AMPA receptors are selectively activated by agonists such as AMPA, glutamic acid, and quisqualic acid. As antagonits against the AMPA receptors, various derivatives of quinoxaline have been developed. Examples of the derivatives include 6,7-dinitroquinoxaline-2,3-dione (DNQX) (Ferrosan), 6-cyano-7-nitroquinoxaline-2,3-dione (CNQX), 2,3-dihydroxy-6-nitro-7-sulfamoylbenzo(f)quinoxaline (NBQX) (Ferrosan), and 6-imidazolyl-7-nitroquinoxaline-2,3-(1H, 4H)-dione (YM900) (Yamanouchi Pharmaceutical Co., Ltd.). Some of these derivatives have been reported in Honore et al., Science, 241, 701–703 (1988); Sheardown et al., Eur. J. Pharmacol., 174, 197–204 (1989), PCT Publication No. WO92-07847, published on May 14, 1992; and Japanese Laid-Open Patent Publication Nos. 63-83074, 63-258466, 1-153680, 2-48578, 2-221263, and 2-221264.

The NMDA receptors have an allosteric site bound by glycine as well as a site recognizing the above-mentioned agonists. It is known that the binding of the allosteric site by glycine remarkably enhances the functions of the NMDA receptors. In recent years, the development of antagonists or modulators which can bind to glycine binding sites, and affect the NMDA receptors allosterically came to public attention. Examples of the antagonist against the glycine binding sites include 5,7-dichlorokynurenic acid HA966 (Eur. J. Pharmacol., 151, 161–163 (1988)).

The above-mentioned DNQX and CNQX have been confirmed to exhibit antagonistic effects on the glycine binding site of the NMDA receptors as well as on the AMPA receptors (Birch et al., Eur. J. Pharmacol., 156, 177–180 (1988); Drejer et al., Neurosci. Lett., 98, 333–338 (1989); Sheardown et al., Science, 247, 571–574 (1990)). Dioxotetrahydroquinolines are also known to exhibit antagonistic effects against both of the glycine binding sites and the AMPA receptors. In general, these compounds exhibit effective antagonistic effects against either one of the NMDA receptors and the AMPA receptors, whereas they do not have effective activities to both of them simultaneously (Larsen et al. ed. EXCITATORY AMINO ACID RECEPTORS, Chapter 11, published by ELLIS HORWOOD (1992)). These compounds have not been put to practical use as central nervines because they are difficult to be transmitted to the brain.

Compounds used as therapeutic agents effective for the above-mentioned diseases and conditions, protecting neurons from death or denaturation caused by the excitatory amino acids, are required to effectively work as antagonists against both the NMDA receptors and the AMPA receptors (Mosinger et al., Exp. Neurol., 113, 10–17 (1991)). Accordingly, there is a demand for compounds having marked antagonistic activities to both the NMDA receptors and the AMPA receptors.

SUMMARY OF THE INVENTION

According to the present invention, the oxopyridinylquinoxaline derivative represented by the following Formula I or pharmaceutically acceptable salts thereof is provided:

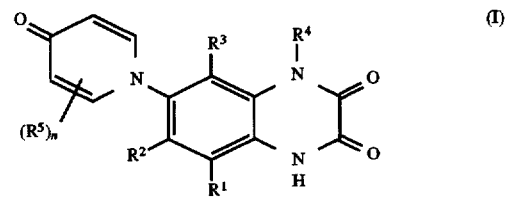

wherein $R^1$ is hydrogen, halogen, nitro, or trihalomethyl; $R^2$ is hydrogen, halogen, nitro, cyano, trihalomethyl, carbamoyl, carbamoyl substituted with lower alkyl, sulfamoyl, or sulfamoyl substituted with lower alkyl; $R^3$ is hydrogen, nitro, or halogen; $R^4$ is hydrogen, lower alkyl, substituted lower alkyl, lower cycloalkyl, or substituted lower cycloalkyl; $R^5$'s are substituents independently selected from the group consisting of halogen, nitro, cyano, lower alkyl, carbamoyl, and carbamoyl substituted with lower alkyl; and n is an integer of 0 to 4.

In one embodiment of the invention, in Formula I, $R^1$ and $R^3$ are independently hydrogen or nitro; $R^2$ is halogen, nitro, cyano, trihalomethyl, carbamoyl, carbamoyl substituted with lower alkyl, sulfamoyl, or sulfamoyl substituted with lower alkyl; $R^4$ is hydrogen or lower alkyl; $R^5$'s are substituents independently selected from the group consisting of halogen, nitro, and lower alkyl; and n is an integer of 0 to 4.

In another embodiment of the invention, in Formula I, each of $R^1$ and $R^3$ is hydrogen; $R^2$ is halogen, nitro, cyano, or trihalomethyl; $R^4$ is hydrogen or lower alkyl; $R^5$'s are substituents independently selected from the group consisting of halogen and nitro; and n is an integer of 0 to 4.

In another embodiment of the invention, in Formula I, n is 0.

In another embodiment of the invention, $R^1$, $R^3$, and $R^4$ in Formula I are independently hydrogen; and $R^2$ is nitro.

A pharmaceutical composition of the present invention includes an oxopyridinylquinoxaline derivative represented by the following Formula I or pharmaceutically acceptable salts thereof as its active component:

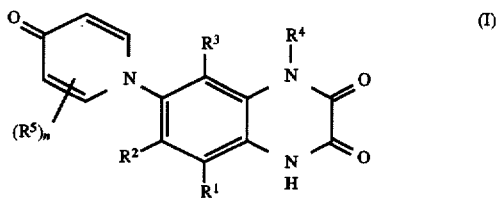

wherein $R^1$ is hydrogen, halogen, nitro, or trihalomethyl; $R^2$ is hydrogen, halogen, nitro, cyano, trihalomethyl, carbamoyl, carbamoyl substituted with lower alkyl, sulfamoyl, or sulfamoyl substituted with lower alkyl; $R^3$ is hydrogen, nitro, or halogen; $R^4$ is hydrogen, lower alkyl, substituted lower alkyl, lower cycloalkyl, or substituted lower cycloalkyl; $R^5$'s are substituents independently selected from the group consisting of halogen, nitro, cyano, lower alkyl, carbamoyl, and carbamoyl substituted with lower alkyl; and n is an integer of 0 to 4.

In one embodiment of the invention, the above-mentioned pharmaceutical composition is for use in competitively inhibiting hyper-stimulation of neurons caused by excitatory amino acids.

In another embodiment of the invention, the above-mentioned pharmaceutical composition has antagonistic activities for glutamate receptor.

In another embodiment of the invention, the above-mentioned pharmaceutical composition is for treating a neurological disease caused by hyper-stimulation of neurons due to excitatory amino acids.

In another embodiment of the invention, the neurological disease is at least one selected from the group consisting of parkinsonism, senile dementia, Huntington's chorea, and epilepsia.

According to another aspect of the invention, a method for competitively inhibiting the hyper-stimulation of neurons by excitatory amino acids, includes administrating, in vivo, a therapeutically effective amount of the above-mentioned compound.

Thus, the invention described herein makes possible the advantages of (1) providing a quinoxaline derivative having outstanding antagonistic activities to a glycine binding site of NMDA receptors and AMPA receptors which are present in the CNS; (2) providing a pharmaceutical composition for use in competitively inhibiting hyper-stimulation of neurons caused by excitatory amino acids; (3) providing a pharmaceutical composition having antagonistic activities to glutamate receptors; (4) providing a pharmaceutical composition for treating neurological disorders caused by hyper-stimulation of neurons due to excessive excitatory amino acids induced by ischemia or anoxia; and (5) providing a method for competitively inhibiting hyper-stimulation of neurons due to excitatory amino acids.

These and other advantages of the present invention will become apparent to those skilled in the art upon reading and understanding the following detailed description.

DESCRIPTION OF THE PREFERRED EMBODIMENTS

The inventors of the present invention found that the following oxopyridinylquinoxaline derivatives generally exhibit antagonistic effects against the glycine binding site of NMDA receptors and AMPA receptors which are present in the CNS. Therefore, oxopyridinylquinoxaline derivatives are effective for the above-mentioned diseases and conditions caused by hyperstimulation of neurons due to excitatory amino acids.

The oxopyridinylquinoxaline derivatives of the present invention are represented by the following Formula I:

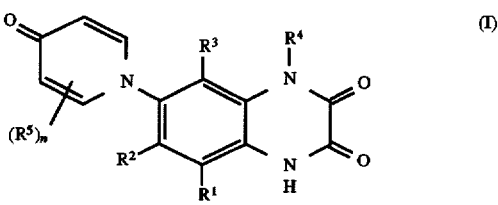

wherein $R^1$ is hydrogen, halogen, nitro, or trihalomethyl; $R^2$ is hydrogen, halogen, nitro, cyano, trihalomethyl, carbamoyl, carbamoyl substituted with lower alkyl, sulfamoyl, or sulfamoyl substituted with lower alkyl; $R^3$ is hydrogen, nitro, or halogen; $R^4$ is hydrogen, lower alkyl, substituted lower alkyl, lower cycloalkyl, or substituted lower cycloalkyl; $R^5$'s are substituents independently selected from the group consisting of halogen, nitro, cyano, lower alkyl, carbamoyl, and carbamoyl substituted with lower alkyl; and n is an integer of 0 to 4 (i.e., n=0, 1, 2, 3 or 4).

In Formula I of the present invention, an oxopyridinyl group, which may be substituted, is introduced into the 6-position or 7-position of quinoxaline, which is novel especially, in terms of structure, and is pharmacologically important.

Examples of halogen include chlorine, fluorine, bromine, and iodine. Examples of trihalomethyl include trifluoromethyl. In the present specification, the lower alkyl refers to a straight-chain or a branched-chain alkyl group having 1 to 6 carbon atoms. Examples of the lower alkyl include methyl, ethyl, butyl, and isopropyl. The lower cycloalkyl refers to a cycloalkyl group having 3 to 6 carbon atoms. Examples of the lower cycloalkyl include cyclopropyl and cyclobutyl.

Examples of the substituted lower alkyl or cycloalkyl represented by $R^4$ include halogen, an amino group, and a carboxyl group.

Preferably, $R^1$ and $R^3$ are independently hydrogen or nitro; more preferably, each of $R^1$ and $R^3$ is hydrogen. Preferably, $R^2$ is halogen, nitro, cyano, trihalomethyl, carbamoyl, carbamoyl substituted with lower alkyl, sulfamoyl, or sulfamoyl substituted with lower alkyl; more preferably, halogen, nitro, cyano, or trihalomethyl; and most preferably, nitro. Preferably, $R^4$ is hydrogen or lower alkyl; and more preferably, hydrogen. Preferably, each of $R^1$, $R^3$, and $R^4$ is hydrogen.

Preferably, $R^5$'s are substituents independently selected from the group consisting of halogen, nitro, and lower alkyl; more preferably, substituents independently selected from the group consisting of halogen and nitro.

The above-mentioned n can be an integer of 0 to 4. In the case where n is 0, any $R^5$ is not present on the oxopyridinyl group. Alternatively, the above-mentioned n can be an integer of 1, 2, 3, or 4. Thus, $(R_5)n$ on the oxopyridinyl group of the oxopyridinylquinoxaline derivatives of the present invention can be a combination of various kinds of substituents and can be present at any position selected from the group consisting of the 2-position, 3-position, 5-position, and 6-position. Examples of $(R^5)n$ include combinations where n is 4 and each of $R_5$'s is halogen; n is 2, each of $R^5$'s is halogen and $R^5$ is present at the 3-position and 5-position; n is 1, $R^5$ is halogen and is present at the 3-position; n is 1, $R^5$ is lower alkyl and is present at the 2-position; and n is 1, $R^5$ is nitro and is present at the 3-position. Preferably, n is 0.

In preferred oxopyridinylquinoxaline derivatives of the present invention, $R^1$ and $R^3$ are independently hydrogen or nitro; $R^2$ is halogen, nitro, cyano, trihalomethyl, carbamoyl, carbamoyl substituted with lower alkyl, sulfamoyl, or sulfamoyl substituted with lower alkyl; $R^4$ is hydrogen or lower alkyl; $R^5$'s are substituents independently selected from the group consisting of halogen, nitro, and lower alkyl; and n is an integer of 0 to 4.

In more preferred oxopyridinylquinoxaline derivatives of the present invention, each of $R^1$ and $R^3$ is hydrogen; $R^2$ is halogen, nitro, cyano, or trihalomethyl; $R^4$ is hydrogen or lower alkyl; $R^5$'s are substituents independently selected from the group consisting of halogen and nitro; and n is an integer of 0 to 4. In still more preferred oxopyridinylquinoxaline derivatives of the present invention, each of $R^1$, $R^3$, and $R^4$ is independently hydrogen; $R^2$ is nitro; and n is 0.

Table 1 shows representative examples of the compound of the present invention.

TABLE 1

| $R^1$ | $R^2$ | $R^3$ | $R^4$ | n | $R^5$ |
|---|---|---|---|---|---|
| H | nitro | H | H | 0 | — |
| H | halogen | H | H | 0 | — |
| H | cyano | H | H | 0 | — |
| H | carbamoyl | H | H | 0 | — |
| H | sulfamoyl | H | H | 0 | — |
| H | trihalomethyl | H | H | 0 | — |
| H | nitro | H | lower alkyl | 0 | — |
| H | halogen | H | lower alkyl | 0 | — |
| H | cyano | H | lower alkyl | 0 | — |
| H | carbamoyl | H | lower alkyl | 0 | — |
| H | sulfamoyl | H | lower alkyl | 0 | — |
| H | trihalomethyl | H | lower alkyl | 0 | — |
| H | nitro | H | H | 1 | methyl at the 2-position |
| H | nitro | H | H | 1 | chlorine at the 3-position |
| H | nitro | H | H | 1 | nitro at the 3-position |
| H | nitro | H | H | 4 | all of $R^5$'s are fluorine |
| H | nitro | H | lower alkyl | 1 | nitro at the 3-position |
| H | sulfamoyl substituted with lower alkyl | H | H | 0 | — |
| nitro | halogen | H | H | 0 | — |
| H | halogen | nitro | H | 0 | — |
| H | nitro | H | H | 1 | fluorine |
| H | trifluoromethyl | H | H | 1 | fluorine |
| H | nitro | nitro | H | 0 | — |

The present invention also includes pharmaceutically acceptable salts of Compound I. Examples of the salts include those of Compound I and inorganic acids such as hydrochloric acid, hydrobromic acid, sulfuric acid, and phosphoric acid; those of Compound I and organic acids such as acetic acid, tartaric acid, fumaric acid, and sulfonic acid; those of Compound I and inorganic bases such as sodium hydroxide and potassium hydroxide; or those of Compound I and organic bases such as tris(hydroxymethyl) aminomethane and choline.

Compound I can be present as stereoisomers and as tautomers depending upon the identity of the substituents to be contained in Compound I. Furthermore, Compound I of the present invention or the salts thereof can be present as a hydrate such as monohydrate and dihydrate. Such hydrates are also within the range of the present invention.

The compounds of the present invention can be produced by Synthetic Process 1 or 2 represented, for example, by the following equation.

(1) Synthetic Process 1

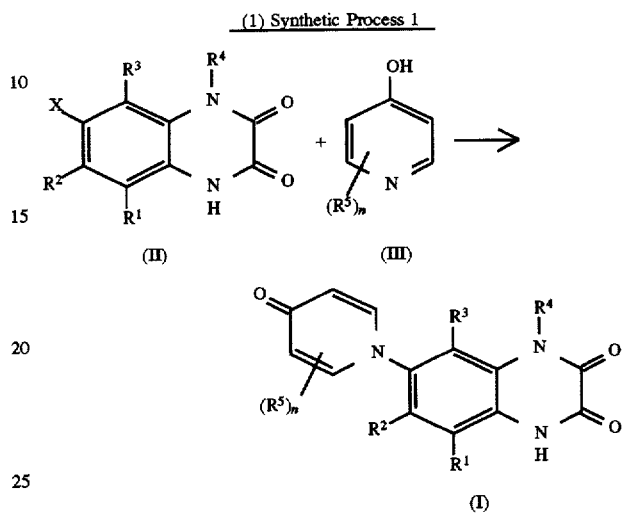

wherein X represents halogen; and $R^1$, $R^2$, $R^3$, $R^4$ and $(R^5)n$ are defined in the same way as in Formula I.

According to this process, haloquinoxaline compound II is reacted with 4-hydroxypyridine compound III. This reaction is generally performed in an organic solvent such as dimethylsulfoxide, dimethylformamide, acetonitrile, acetone, and terahydrofuran, preferably at a temperature of about 80° to 180° C. Various bases can be added for the purpose of promoting the reaction. Examples of the preferred bases include sodium hydroxide, potassium hydroxide, and potassium carbonate.

(2) Synthetic Process 2

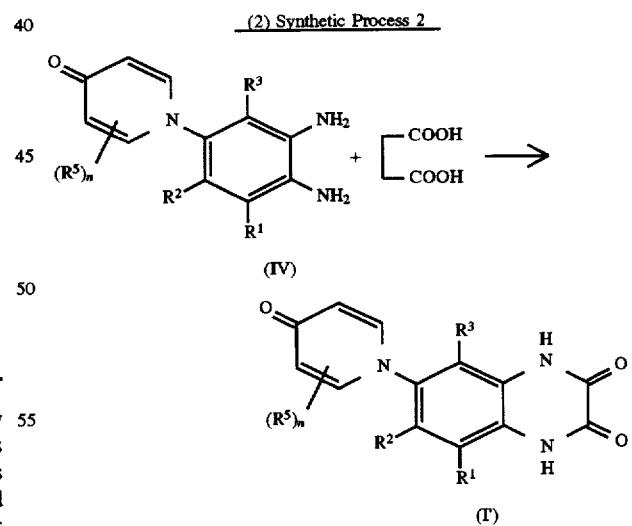

wherein $R^1$, $R^2$, $R^3$, and $(R^5)n$ are defined in the same way as in Formula I.

According to this process, oxopyridinyl-o-phenylenediamine derivative IV is reacted with an equimolar or excess molar amount of oxalic acid at room temperature or higher. A reactive derivative of oxalic aid can be used in this reaction in place of oxalic acid. Examples of the preferred derivatives include salts, esters, hydrates, anhydrides, and acid chlorides. This reaction is generally effected in an aqueous or alcohol solvent. Various acids can be added for the purpose of promoting the reaction. An example of the preferred acid is hydrochloric acid. Compound I' obtained by this reaction corresponds to Formula I of the present invention, where $R^4$ is hydrogen.

The compounds of the present invention can also be produced by introducing a new substituent into the compounds obtained by the above-mentioned process or substituting the compounds with a suitable substituent. For example, Compound I-2 of the present invention where $R^2$ is nitro can be obtained by nitrating Compound I-1 of the present invention where $R^2$ is hydrogen, as represented by the following equation.

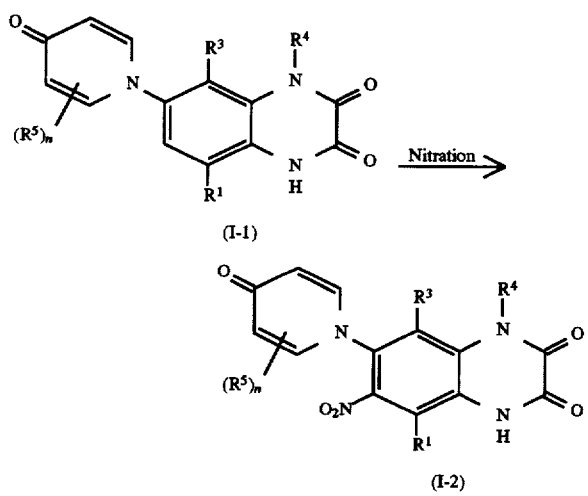

wherein $R^1$, $R^3$, $R^4$, and $(R^5)n$ are defined in the same way as in Formula I.

Nitration can be effected by treating Compound I-1 of the present invention where $R^2$ is hydrogen with nitric acid or one of its salts under acidic conditions of sulfuric acid or acetic anhydride-acetic acid. Alternatively, the nitration can be effected by heating Compound I-1 in an organic solvent such as sulfolane together with nitronium tetrafluoroborate.

Alternatively, as represented by the following equation, the compounds of the present invention can be obtained by treating Compound I-3 with chlorosulfonic acid or its salts so as to introduce a chlorosulfonyl group, and further treating the resultant compound with ammonia or an ammonium salt so as to introduce sulfamoyl as $R^2$ under the similar acidic conditions as the above.

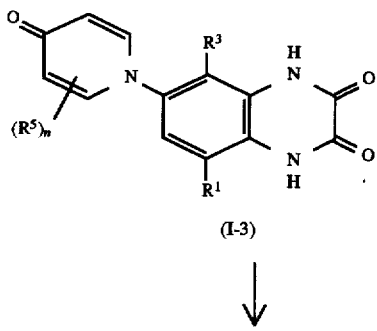

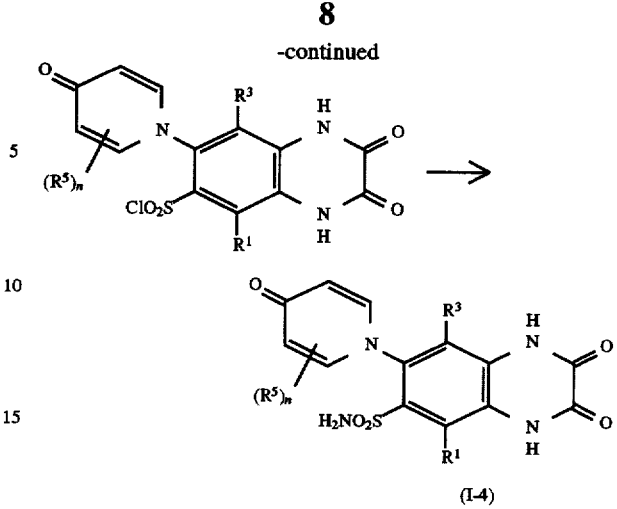

The ability of the compound of the present invention to bind to these receptors can be measured by the competitive assay using glycine or AMPA labeled with $^3H$. Furthermore, experiments using rats confirmed that the compounds of the present invention exhibit a protective function for neurological disorders.

The ability of the compounds of the present invention to bind to a glycine binding site of the NMDA receptors can be measured, for example, using competitive assay in vitro as described below.

A rat cerebral cortex is homogenized with a buffer solution, and repeatedly centrifuged and resuspended in a buffer to prepare a membrane sample. The membrane sample is mixed with a solution containing [$^3H$] glycine and a compound of interest and incubated for a predetermined period of time. Then, the reaction of the mixture is terminated by dilution and filtration using filter paper. Radioactivity on the filter paper is measured by a liquid scintillation counter. Non-specific binding is measured with 1 mM of non-radioactive glycine to work out $IC_{50}$.

The binding ability of the compounds of the present invention with respect to the AMPA receptors can be measured, for example, by the following competitive assay.

A rat cerebral cortex is homogenized with a buffer solution, and repeatedly centrifuged and resuspended in a buffer to prepare a membrane sample. The membrane sample is mixed with a solution containing [$^3H$] AMPA and a compound of interest and incubated for a predetermined period of time. Then, the reaction of the mixture is terminated by dilution and filtration using filter paper. Radioactivity on the filter paper is measured by a liquid scintillation counter. Non-specific binding is measured with 1 mM of non-radioactive glutamate to work out $IC_{50}$.

A composition containing oxopyridinylquinoxaline derivatives of the present invention can be therapeutic agents effective for neurological disorders caused by the binding of excitatory amino acids to the NMDA receptors, especially to a glycine binding site and to the AMPA receptors. The composition can be orally or non-orally administered to subjects. The pharmaceutical composition in the form of an injectable solution or a suspension, preferably in the form of an aqueous solution are suitable for non-oral administration; those in the form of a tablet and a capsule are suitable for oral administration. These compositions can contain a compound of the present invention in various concentrations. Pharmaceutically acceptable organic or inorganic excipient such as salines, alcohols, castor oil, gelatin, lactose, starch, and talc can be contained in the composition.

Furthermore, if desired, various auxiliary substances such as a lubricant, a stabilizer, and an emulsifier can be contained in the composition.

The dose of the composition of the present invention as a therapeutic agent can be varied depending upon age, weight, conditions, therapeutic effects, a method for administration, a treating time, etc. of subjects. The composition can be administered to human beings orally or parenterally, especially intravenously. In the case of an adult, the composition is generally administered orally at a dose of about 1 to 1000 mg preferably 10 to 500 mg per day; or parenterally at dose of about 1 to 500 mg per day; in one to several divided doses or continuously in terms of the oxopyridinyl quinoxaline derivative of Formula I.

EXAMPLES

Hereinafter, the present invention will be described in detail by way of illustrative examples. It should be noted that the present invention is not limited by the following examples.

In the examples, NMR denotes nuclear magnetic resonance spectroscopy and IR denotes infrared spectroscopy.

Reference Examples 1 to 6 will show production examples of compounds used for starting materials in the examples of the present invention.

REFERENCE EXAMPLE 1

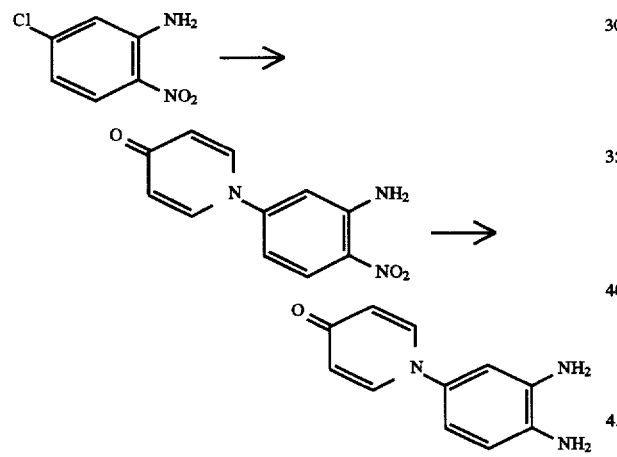

2-Nitro-5-(4-oxo-4H-pyridin-1-yl)-aniline

First, 8.628 g of 5-chloro-2-nitroaniline, 7.161 g of 4-hydroxypyridine, and 4.892 g of powdered potassium hydroxide were added to 60 ml of dry dimethylsulfoxide The mixture thus obtained was stirred at 130° C. for 3 hours in a nitrogen atmosphere. Then, 200 ml of ice water was added to the reaction mixture and neutralized with 4N hydrochloric acid. The resultant solution was stirred for 30 minutes, giving a precipitate. The precipitate was filtered and washed with water. The precipitate was subjected to silica gel column chromatography, and fractions eluted with 20% methanol in methylene chloride were collected. The collected fractions were combined and evaporated. The residue was recrystallized in methanol to give 11.868 g of yellowish orange crystals of 2-nitro-5-(4-oxo-4H-pyridin-1-yl)-aniline.

Melting point: 298°–303° C. Elemental analysis (analyzed as $C_{11}H_9N_3O_3 \cdot \frac{1}{3}H_2O$) Calculated: C,56.27; H,4.03; N,17.90 (%) Found: C,56.21; H,4.01; N,17.79 (%) $H^1$-NMR ($d_6$-DMSO) δ: 6.26 (2H, d, J=7.8 Hz), 6.81 (1H, dd, J=9.4, 2.8 Hz), 7.08 (1H, d, J=2.8 Hz), 7.61 (2H, br.s), 7.99 (2H, d, J=7.8 Hz), 8.12 (1H, d, J=9.4 Hz).

4-(4-Oxo-4H-pyridin-1-yl)-1,2-phenylenediamine

First, 5.515 g of 2-nitro-5-(4-oxo-4H-pyridin-1-yl)-aniline was added to a suspension containing 7.975 g of iron powder, 20 ml of water, and 78 ml of ethanol, followed by adding 2 ml of 2N hydrochloric acid. The resultant mixture was refluxed by heating for 6 hours. Then, 1.092 g of iron powder and 2 ml of 2N hydrochloric acid were added to the mixture. The resultant mixture was refluxed for another 1 hour. After the reaction, the reaction mixture was hot filtered using celite, and a residue on the celite was thoroughly washed with warm ethanol. The mother liquor and the washings were combined together and concentrated to dryness. The residue thus obtained was subjected to silica gel column chromatography, and fractions eluted with 5% methanol in chloroform were collected. The collected fractions were combined and evaporated. The residue was recrystallized with isopropanol-methanol (1:1) to give 4.137 g of orange crystals of 4-(4-oxo-4H-pyridin-1-yl)-1,2-phenylenediamine.

Melting point: 257°–259.5° C. Elemental analysis (analyzed as $C_{11}H_{11}N_3O$) Calculated: C,65.66; H,5.51; N,20.88 (%) Found: C,65.51; H,5.58; N,20.63 (%) $H^1$-NMR ($d_6$-DMSO)δ: 4.76 (2H, br.s), 4.85 (2H, br.s), 6.15 (2H, d, J=7.6 Hz), 6.46 (1H, dd, J=8.2, 2.4 Hz), 6.57 (2H, m), 7.75 (2H, d, J=7.6 Hz).

REFERENCE EXAMPLE 2

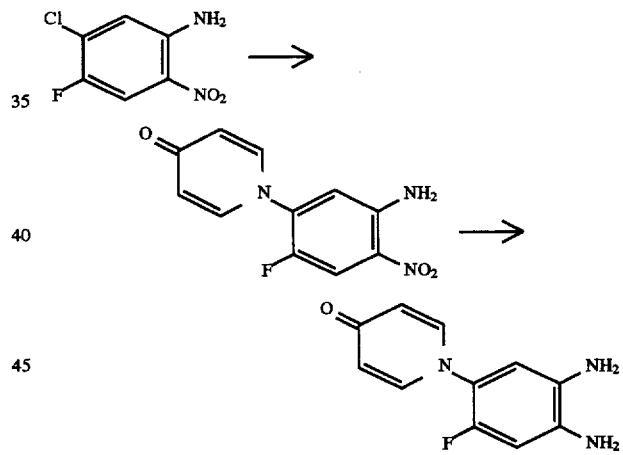

2-Nitro-4-fluoro-5-(4-oxo-4H-pyridin-1-yl)-aniline

First, 3.811 g of 2-nitro-4-fluoro-5-chloroaniline, 2.473 g of 4-hydroxypyridine, and 1.827 g of powdered potassium hydroxide were allowed to react at 130° C. for 3 hours in a nitrogen atmosphere in the same way as in Reference Example 1 to give 1.125 g of 2-nitro-4-fluoro-5-(4-oxo-4H-pyridin-1-yl)-aniline.

Melting point: >305° C. (decomposition) Elemental analysis (analyzed as $C_{11}H_8N_3O_3F$) Calculated: C,53.02; H,3.24; N,16.86; F,7.62 (%) Found: C,52.63; H,3.46; N,16.64; F, 7.44 (%) $H^1$-NMR ($d_6$-DMSO)δ: 6.27 (2H, d, J=7.8 Hz), 7.18 (1H, d, $J_{FH}$=7.0 Hz), 7.57 (2H, br.s), 7.87 (2H, d, J=7.8 Hz), 8.07 (1H, d, $J_{FH}$=11.2 Hz).

4-Fluoro-5-(4-oxo-4H-pyridin-1-yl)-1,2-phenylenediamine

First, 1.065 g of 2-nitro-4-fluoro-5-(4-oxo-4H-pyridin-1-yl)-aniline was dissolved in 45 ml of dimethylformaldehyde by heating and reduced over 195 mg of 10% paradium-carbon catalyst under atmospheric pressure. After the reaction, the reaction mixture was filtered through celite to remove the catalyst, and the mother liquor thus obtained was concentrated to dryness. The residue thus obtained was subjected to column chromatography using 30 g of silica gel, and fractions eluted with a methylene chloride-methanol (20:1) solution were collected. The collected fractions were combined and evaporated. The residue was recrystallized with ethanol to give 802 mg of 4-fluoro-5-(4-oxo-4H-pyridin-1-yl)-1,2-phenylenediamine.

Melting point: 227°–229.5° C. Elemental analysis (analyzed as $C_{11}H_{10}N_3OF$) Calculated: C,60.27; H,4.60; N, 19.17; F, 8.67 (%) Found: C,60.38; H,4.76; N,19.01; F,8.62 (%) $H^1$-NMR ($d_6$-DMSO)δ: 6.24(2H, d, J=7.8 Hz), 6.50 (1H, d, $J_{FH}$=12.6 Hz), 6.58 (1H, d, $J_{FH}$=7.8 Hz), 7.70 (2H, d, J=7.8 Hz).

REFERENCE EXAMPLE 3

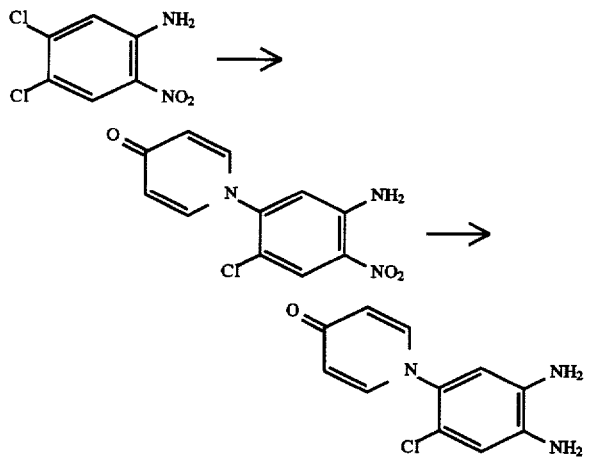

4-Chloro-3-(4-oxo-4H-pyridin-1-yl)-6-nitroaniline

First, a mixture containing 14.3 g of 3,4-dichloro-6-nitroaniline, 9.01 g of 4-hydroxypyridine, 5.87 g of 86% potassium hydroxide, and 70 ml of dimethylsulfoxide was heated in an oil bath at 130° C. for 3.5 hours, and cooled. Ice water was added to the mixture and precipitated crystals were filtered. Then, 16.9 g of the resultant crude crystals were applied to a column containing 100 g of silica gel and eluted with 10% methanol in chloroform. The eluate was combined and evaporated. The residue was filtered to give 9.78 g of crude crystals of 4-chloro-3-(4-oxo-4H-pyridin-1-yl)-6-nitroaniline (melting point: 288° to 291° C. (decomposition)). Then, 300 mg of the crude crystals were recrystallized with methanol to give 268 mg of crystals of 4-chloro-3-(4-oxo-4H-pyridin-1-yl)-6-nitroaniline.

Melting point: 290°–293° C. (decomposition) Elemental analysis (analyzed as $C_{11}H_8N_3O_3Cl$) Calculated: C,49.73; H,3.04; N,15.82; Cl,13.35 (%) Found: C,49.52; H,3.20; N,15.66; Cl,13.08 (%) $H^1$-NMR ($d_6$-DMSO)δ: 6.22 (2H, dd, J=6 Hz, J=2 Hz), 7.19 (1H, s), 7.73(2H, br.s), 7.78(2H, dd, J=6 Hz, J=2 Hz), 8.23(1H, s).

4-Chloro-5-(4-oxo-4H-pyridin-1-yl)-1,2-phenylenediamine

First, a mixture containing 3.0 g of 4-chloro-3-(4-oxo-4H-pyridin-1-yl)-6-nitroaniline, 3.78 g of iron powder, 10 ml of water, 90 ml of ethanol, and 1.15 ml of 2N hydrochloric acid was refluxed by heating in an oil bath for 3 hours. Then, 135 ml of ethanol was added to the mixture, and insoluble substances were filtered with Hyflo Super-Cel (trade name) and the solvent was removed.

Crude crystals thus obtained were applied to a column containing 30 g of silica gel and eluted with 20% methanol in chloroform. The eluate was combined and evaporated. The residue was recrystallized with methanol/isopropanol to give 2.04 g of crystals of 4-chloro-5-(4-oxo-4H-pyridin-1-yl)-1,2-phenylenediamine.

Melting point: 260°–261° C. (decomposition) Elemental analysis (analyzed as $C_{11}H_{10}N_3OCl$) Calculated: C,56.06; H,4.28; N,17.83; Cl,15.05 (%) Found: C,56.05; H,4.30; N,17.75; Cl,15.17 (%) $H^1$-NMR ($d_6$-DMSO)δ: 4.97 (2H, s), 5.12 (2H, s), 6.12 (2H, d, J=8 Hz), 6.58 (1H, s), 6.64 (1H, s), 7.57 (2H, d, J=8 Hz).

REFERENCE EXAMPLE 4

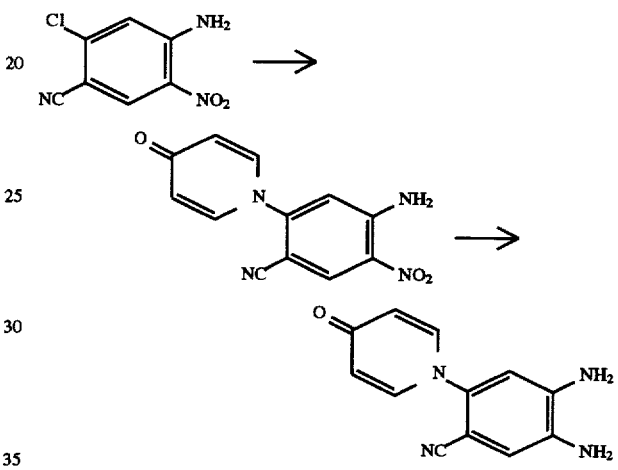

4-Cyano-3-(4-oxo-4H-pyridin-1-yl)-6-nitroaniline

First, a mixture containing 1.0 g of 3-chloro-4-cyano-6-nitroaniline, 507 mg of 4-hydroxypyridine, 330 mg of 86% potassium hydroxide, and 5 ml of dimethylsulfoxide was heated in an oil bath at 110° C. for 3 hours. The subsequent processes were conducted in the same way as in Reference Example 3 to give 836 mg of crystals of 4-cyano-3-(4-oxo-4H-pyridin-1-yl)-6-nitroaniline.

Melting point: 354°–357° C. (decomposition) Elemental analysis (analyzed as $C_{12}H_8N_4O_3$) Calculated: C,56.25; H,3.15; N,21.87 (%) Found: C,56.25; H,3.27; N,21.83 (%) $H^1$-NMR ($d_6$-DMSO)δ: 6.28 (2H, d, J=8 Hz), 7.13 (1H, s), 7.92 (2H, d, J=8 Hz), 8.24 (2H, br.s), 8.68 (1H, s).

4-Cyano-5-(4-oxo-4H-pyridin-1-yl)-1,2-phenylenediamine

First, a mixture containing 490 mg of 4-cyano-3-(4-oxo-4H-pyridin-1-yl)-6-nitroaniline, 642 mg of iron powder, 4 ml of water, 16 ml of ethanol, and 0.2 ml of 2N hydrochloric acid was heated in an oil bath for 1 hour. The subsequent processes were conducted in the same way as in Reference Example 3 to give crude crystals. Then, 405 mg of the crude crystals were recrystallized with methanol/isopropanol to give 274 mg of crystals of 4-cyano-5-(4-oxo-4H-pyridin-1-yl)-1,2-phenylenediamine.

Melting point: 321°–323° C. (decomposition) Elemental analysis (analyzed as $C_{12}H_{10}N_4O$) Calculated: C,63.70; H,4.46; N,24.77 (%) Found: C,63.57; H,4.59; N,24.41 (%) $H^1$-NMR ($d_6$-DMSO)δ: 5.21 (2H, s), 5.90 (2H, s), 6.17 (2H, d, J=8 Hz), 6.59 (1H, s), 6.82 (1H, s), 7.73 (2H, d, J=8 Hz).

REFERENCE EXAMPLE 5

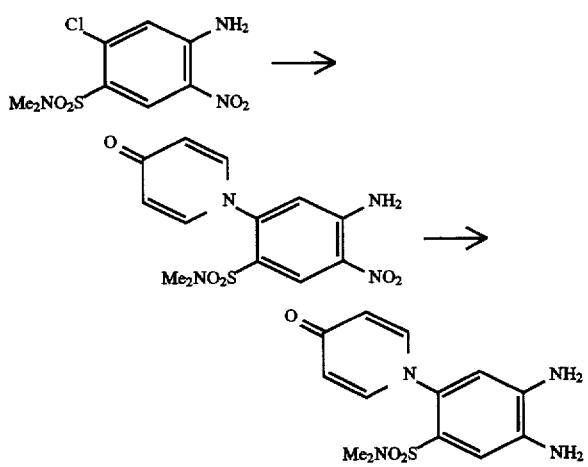

4-Dimethylsulfamoyl-3-(4-oxo-4H-pyridin-1-yl)-6-nitroaniline

First, a mixture containing 3.0 g of 3-chloro-4-dimethylsulfamoyl-6-nitroaniline, 1.39 g of 4-hydroxypyridine, 0.91 g of 86% potassium hydroxide, and 20 ml of dimethylsulfoxide was heated in an oil bath at 130° C. for 1.5 hours. The subsequent processes were conducted in the same way as in Reference Example 3 to give 1.675 g of 4-dimethylsulfamoyl-3-(4-oxo-4H-pyridin-1-yl)-6-nitroaniline.

Melting point: 344°–347° C. (decomposition) Elemental analysis (analyzed as $C_{13}H_{14}N_4O_5S$) Calculated: C,46.15; H,4.17; N,16.56; S,9.48 (%) Found: C,46.11; H,4.22; N,16.36; S,9.37 (%) $H^1$-NMR ($d_6$-DMSO)δ: 2.56 (6H, s), 6.16 (2H, d, J=8 Hz), 7.09 (1H, s), 7.71 (2H, d, J=8 Hz), 8.25 (2H, br.s), 8.51 (1H, s).

4-Dimethylsulfamoyl-5-(4-oxo-4H-pyridin-1-yl)-1,2-phenylenediamine

First, a mixture containing 1.50 g of 4-dimethylsulfamoyl-3-(4-oxo-4H-pyridin-1-yl)-6-nitroaniline, 1.49 g of iron powder, 9 ml of water, 36 ml of ethanol, and 0.45 ml of 2N hydrochloric acid was refluxed by heating in an oil bath for 45 minutes. The subsequent processes were conducted in the same way as in Reference Example 3 to give crude crystals. The crude crystals were recrystallized with methanol/isopropanol to give 1.30 g of crystals of 4-dimethylsulfamoyl-5-(4-oxo-4H-pyridin-1-yl)-1,2-phenylenediamine.

Melting point: 334°–336° C. (decomposition) Elemental analysis (analyzed as $C_{13}H_{16}N_4O_3S$) Calculated: C,50.63; H,5.23; N,18.17; S,10.40 (%) Found: C,50.43; H, 5.28; N, 18.16; S,10.58 $H^1$-NMR ($d_6$-DMSO)δ: 2.51 (6H, s), 5.21 (2H, s), 5.90 (2H, s), 6.17 (2H, d, J=8 Hz), 6.59 (1H, s), 6.82 (1H, s), 7.73 (2H, d, J=8 Hz).

REFERENCE EXAMPLE 6

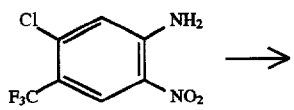

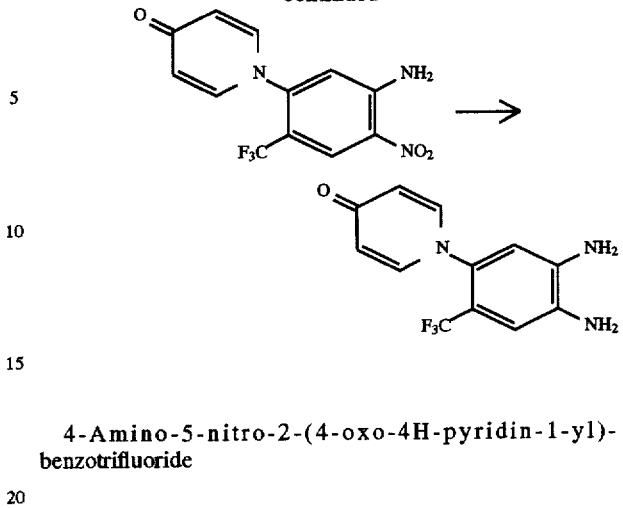

4-Amino-5-nitro-2-(4-oxo-4H-pyridin-1-yl)-benzotrifluoride

First, a mixture containing 2.40 g of 4-amino-2-chloro-5-nitrobenzotrifluoride, 2.0 g of 4-hydroxypyridine, 684 mg of 86% potassium hydroxide, 15 ml of dimethylsulfoxide was heated in an oil bath at 70° C. for 2 hours. The mixture was cooled and ice water was added to the mixture. Precipitated crude crystals were filtered and recrystallized with methanol/ethyl acetate to give 2.69 g of crystals of 4-amino-5-nitro-2-(4-oxo-4H-pyridin-1-yl)-benzotrifluoride.

Melting point: 274°–275° C. Elemental analysis (analyzed as $C_{12}H_8N_3O_3F_3$) Calculated: C,48.17; H,2.70; N,14.04; F,19.05 (%) Found: C,48.12; H,2.78; N,13.98; F,19.11 (%) $H^1$-NMR ($d_6$-DMSO)δ: 6.19 (2H, d, J=8 Hz), 7.17 (1H, s), 7.74 (2H, d, J=8 Hz), 8.17 (2H, br.s), 8.38 (1H, s).

4-(4-Oxo-4H-pyridin-1-yl)-5-trifluoromethyl-1,2-phenylenediamine

First, a mixture containing 2.56 g of 4-amino-5-nitro-2-(4-oxo-4H-pyridin-1-yl)-benzotrifluoride, 2.87 g of iron powder, 14.4 ml of water, 57.6 ml of ethanol, and 0.86 ml of 2N hydrochloric acid was refluxed by heating in an oil bath for 45 minutes. The subsequent processes were conducted in the same way as in Reference Example 3 to give 1.73 g of crystals of 4-(4-oxo-4H-pyridin-1-yl)-5-trifluoromethyl-1,2-phenylenediamine.

Melting point: 264°–266° C. (decomposition) Elemental analysis (analyzed as $C_{12}H_{10}N_3OF_3$) Calculated: C,53.53; H,3.74; N,15.61; F,21.17 (%) Found: C,53.55; H,3.87; N,15.52; F,21.30 (%) $H^1$-NMR ($d_6$-DMSO)δ: 5.23 (2H, br.s), 5.53 (2H, br.s), 7.57 (2H, d, J=8 Hz), 6.09 (2H, d, J=8 Hz), 6.54 (1H, s), 6.86 (1H, s).

EXAMPLE 1

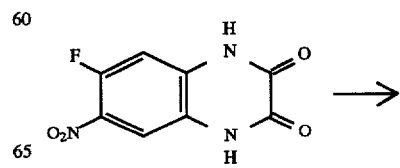

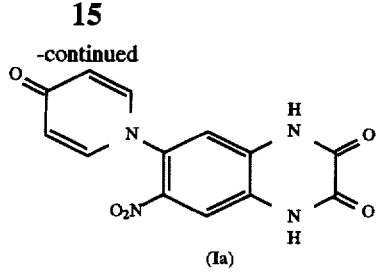

(Ia)

6-Nitro-7-(4-oxo-4H-pyridin-1-yl)-1,4-dihydroquinoxaline-2,3-dione

First, 9.007 g of 7-fluoro-6-nitro-1,4-dihydroquinoxaline-2,3-dione, 7.611 g of 4-hydroxypyridine, and 5.219 g of powdered potassium hydroxide were added to 120 ml of dry dimethylsulfoxide. The mixture was stirred at 130° C. for 2 hours in a nitrogen atmosphere. Then, 50 ml of ice water and 30 ml of 4N hydrochloric acid were added to the reaction mixture so as to make it weakly acidic (pH 3 to 4). The resultant yellow precipitate was filtered and washed with water. The precipitate was dissolved by heating in a mixture containing 560 ml of water and 56 ml of conc. aqueous ammonia. One gram of activated carbon was added to the resultant mixture, stirred, and filtered. The filtrate was neutralized with conc. hydrochloric acid and ice-cooled. The precipitated crystals were then filtered and washed with water, methanol, and ethanol, successively. The resultant crystals were dried to give 7.56 g of 6-nitro-7-(4-oxo-4H-pyridin-1-yl)-1,4-dihydroquinoxaline-2,3-dione (hereinafter, abbreviated as Ia).

Melting point: >300° C. Elemental analysis (analyzed as $C_{13}H_8N_4O_5$) Calculated: C,52.01; H,2.69; N,18.66 (%) Found: C,51.83; H,2.89; N,18.69 (%) $H^1$-NMR ($d_6$-DMSO) δ: 6.22 (2H, d, J=7.4 Hz), 7.21 (1H, s), 7.78 (2H, d, J=7.4 Hz), 8.00 (1H, s) IR (Nujol): 3080, 2920, 2580, 1730, 1695, 1635, 1595 $cm^{-1}$.

Sulfate of Compound Ia: Melting point: >300° C. Elemental analysis (analyzed as $C_{13}H_8N_4O_5 \cdot \frac{1}{2}H_2SO_4 \cdot H_2O$) Calculated: C,42.51; H,3.02; N,15.25; S,4.36 (%) Found: C,42.27; H,3.10; N,15.65; S,4.36 (%) $H^1$-NMR ($d_6$-DMSO) δ: 6.81 (2H, d, J=7.6 Hz), 7.33 (1H, s), 8.05 (1H, s), 8.30 (2H, d, J=7.4 Hz).

A choline salt of Compound Ia is obtained as follows.

First, 2.70 g (9.0 mmol) of 6-nitro-7-(4-oxo-4H-pyridin-1-yl)-1,4-dihydroquinoxaline-2,3-dione was added to 30 ml of acetone and stirred. Then, 2.25 ml (10.0 mmol, 1.1 equivalents) of 50% aqueous solution of choline hydroxide was added to the mixture and stirred. The mixture was allowed to stand for 1.5 hours, and the precipitate thus formed was filtered and washed with acetone. The resultant reddish orange precipitate was dissolved by heating in 200 ml of ethanol. The solution was treated with activated carbon and filtered. The filtrate was concentrated to three-forths of its original volume and allowed to cool. The precipitated crystals were filtered to give 3.58 g of crystals of a choline salt in an 88.9% yield.

Melting point: 230°–233° C. Elemental analysis (analyzed as $C_{13}H_7N_4O_5 \cdot C_5H_{14}NO \cdot 2.5 \, H_2O$) Calculated: C,48.21; H,5.84; N, 15.62; $H_2O$,10.04 (%) Found: C,48.40; H,5.80; N,15.86; $H_2O$,10.20 (%) $H^1$-NMR ($d_6$-DMSO)δ: 3.11 (9H, s), 3.41 (2H, t, J=4.6 Hz), 3.85 (2H, m), 6.14 (2H, d, J=7.4 Hz), 6.87 (1H, s), 7.71 (2H, d, J=7.8 Hz), 7.82 (1H, s).

EXAMPLE 2

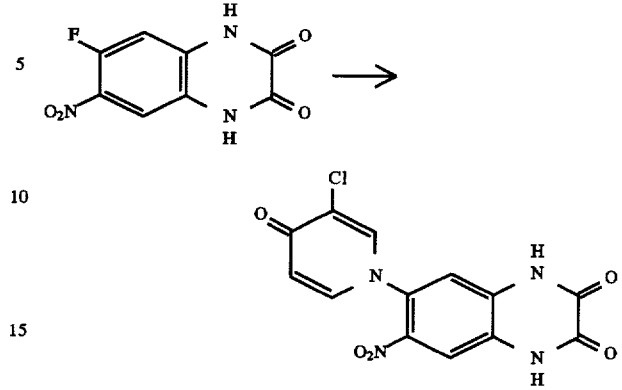

6-Nitro-7-(3-chloro-4-oxo-4H-pyridin-1-yl)-1,4-dihydroquinoxaline-2,3-dione

First, 267 mg of 7-fluoro-6-nitro-1,4-dihydroquinoxaline-2,3-dione, 171 mg of 3-chloro-4-hydroxypyridine, and 92 mg of powdered potassium hydroxide were added to 3 ml of dry dimethylsulfoxide. The mixture was allowed to react at 130° C. for 80 minutes in a nitrogen atmosphere. Ice water and 4N hydrochloric acid were then added to the reaction mixture so as to adjust its pH to about 2. The resultant yellow precipitate was filtered and washed with water. The precipitate was recrystallized with a mixture of dimethylformaldehyde and water to give 376 mg of yellowish white 6-nitro-7-(3-chloro-4-oxo-4H-pyridin-1-yl)-1,4-dihydroquinoxaline-2,3-dione.

Melting point: >300° C. Elemental analysis (analyzed as $C_{13}H_7N_4O_5Cl \cdot C_3H_7NO \cdot H_2O$) Calculated: C,45.13; H,3.79; N,16.45; Cl,8.33 (%) Found: C,45.14; H,3.46; N, 16.33; Cl, 8.57 (%) $H^1$-NMR ($d_6$-DMSO)δ: 6.38 (1H, d, J=7.8 Hz), 7.27 (1H, s), 7.86 (1H, dd, J=7.8, 2.4 Hz), 8.02 (1H, s), 8.42 (1H, d, J=2.4 Hz), 12.43 (2H, br. s).

EXAMPLE 3

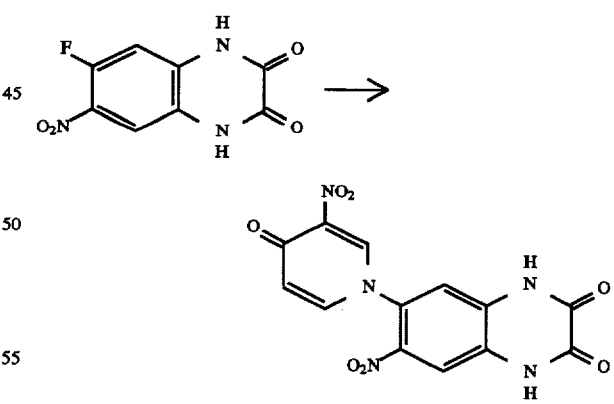

6-Nitro-7-(3-nitro-4-oxo-4H-pyridin-1-yl-)-1,4-dihydroquinoxaline-2,3-dione

First, 677 mg of 7-fluoro-6-nitro-1,4-dihydroquinoxaline-2,3-dione, 840 mg of 4-hydroxy-3-nitropyridine, 403 mg of powdered potassium hydroxide were added to 6 ml of dry dimethylsulfoxide. The mixture was allowed to react at 130° C. for 2 hours in a nitrogen atmosphere. The subsequent processes were conducted in the same way as in Example 2. The resultant precipitate was recrystallized with dimethylformaldehyde and water, giving 672 mg of red crystals of 6-nitro-7-(3-nitro-4-oxo-4H-pyridin-1-yl)-1,4-dihydroquinoxaline-2,3-dione.

Melting point: >300° C. Elemental analysis (analyzed as $C_{13}H_7N_5O_7$) Calculated: C,45.23; H,2.04; N,20.29 (%) Found: C,45.25; H,2.82; N,20.20 (%) $H^1$-NMR ($d_6$-DMSO) δ: 6.62 (1H, d, J=7.8 Hz), 7.40 (1H, s), 7.96 (1H, dd, J=7.8, 2.0 Hz), 8.06 (1H, s), 9.11 (1H, d, J=2.0 Hz).

EXAMPLE 4

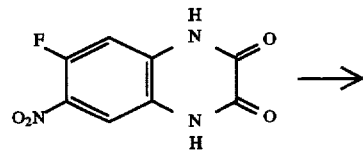

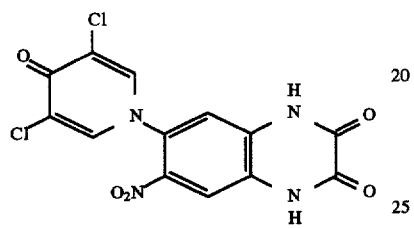

6-Nitro-7-(3,5-dichloro-4-oxo-4H-pyridin-1-yl)-1,4-dihydroquinoxaline-2,3-dione

First, 1.129 g of 7-fluoro-6-nitro-1,4-dihydroquinoxaline-2,3-dione, 1.648 g of 3,5-dichloro-4-hydroxypyridine, and 672 mg of powdered potassium hydroxide were added to 10 ml of dry dimethylsulfoxide. The mixture was allowed to react at 130° C. for 3 hours in a nitrogen atmosphere. The subsequent processes were conducted in the same way as in Example 2. The resultant precipitate was dissolved by heating in dimethylformaldehyde and the solution was decolorized with activated carbon and filtered. Water in an equal amount was added thereto and the solution was allowed to stand overnight to give 1.473 g of crystals of 6-nitro-7-(3,5-dichloro-4-oxo-4H-pyridin-1-yl)-1,4-dihydroquinoxaline-2,3-dione.

Melting point: >300° C. Elemental analysis (analyzed as $C_{13}H_6N_4O_5Cl_2·½H_2O$) Calculated: C,41.29; H,1.87; N,14.82; Cl,18.75 (%) Found: C,41.47; H,1.84; N,15.08; Cl,19.01 (%) $H^1$-NMR ($d_6$-DMSO)δ:7.39 (1H, s), 8.06 (1H, s), 8.55 (2H, s).

EXAMPLE 5

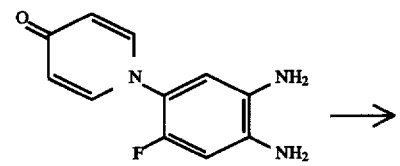

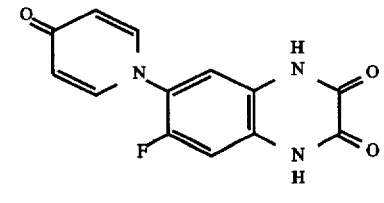

6-Fluoro-7-(4-oxo-4H-pyridin-1-yl)-1,4-dihydroquinoxaline-2,3-dione

First, 4.266 g of 4-fluoro-5-(4-oxo-4H-pyridin-1-yl)-1,2-phenylenediamine, and 1.927 g of oxalic acid were added to 48 ml of 4N hydrochloric acid. The mixture was refluxed by heating for 2.5 hours. After the reaction, precipitated crystals were filtered, washed with water, and dried to give 3.920 g of 6-fluoro-7-(4-oxo-4H-pyridin-1-yl)-1,4-dihydroquinoxaline-2,3-dione.

Melting point: >300° C. Elemental analysis (analyzed as $C_{13}H_8N_3O_3F·0.2H_2O$) Calculated: C,56.40; H,3.06; N,15.18; F,6.86 (%) Found: C,56.21; H,3.19; N,15.24; F,6.93 (%) $H^1$-NMR ($d_6$-DMSO)δ: 6.23 (2H, d, J=7.8 Hz), 7.13 (1H, d, $J_{FH}$=16 Hz), 7.17 (1H, d, $J_{FH}$=12.6 Hz), 7.80 (1H, d, J=6.4 Hz), 12.09 (1H, br.s), 12.15 (1H, br.s).

EXAMPLE 6

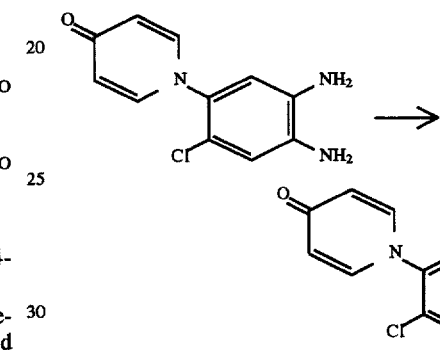

6-Chloro-7-(4-oxo-4H-pyridin-1-yl)-1,4-dihydroquinoxaline-2,3-dione

First, a mixture containing 1.93 g of 4-chloro-5-(4-oxo-4H-pyridin-1-yl)-1,2-phenylenediamine, 2.21 g of oxalic acid, and 40 ml of 2N hydrochloric acid was refluxed by heating in an oil bath for 2 hours. The mixture was cooled and precipitated crystals were filtered to give 2.1 g of crude crystals of 6-chloro-7-(4-oxo-4H-pyridin-1-yl)-1,4-dihydroquinoxaline-2,3-dione (melting point: >400° C.). Then, 500 mg of the crude crystals were recrystallized with dimethylformaldehyde and water to give 299 mg of 6-chloro-7-(4-oxo-4H-pyridin-1-yl)-1,4-dihydroquinoxaline-2,3-dione.

Melting point: 420°–445° C. (decomposition) Elemental analysis (analyzed as $C_{13}H_8N_3O_3Cl·¼H_2O$) Calculated: C,53.07; H,2.91; N,14.28; Cl,12.05 (%) Found: C,53.09; H,2.83; N,14.24; Cl,12.36 (%) $H^1$-NMR ($D_2O$-$HNO_3$)δ: 7.46 (2H, d, J=8 Hz), 7.57 (1H, s), 7.59 (1H, s), 8.57 (2H, d, J=8 Hz).

EXAMPLE 7

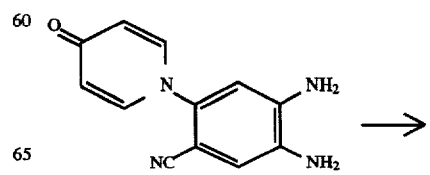

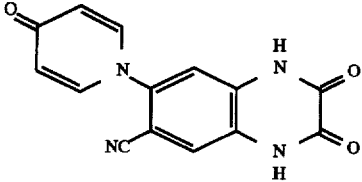

6-Cyano-7-(4-oxo-4H-pyridin-1-yl)-1,4-dihydroquinoxaline-2,3-dione

First, a mixture containing 246 mg of 4-cyano-5-(4-oxo-4H-pyridin-1-yl)-1,2-phenylenediamine, 294 mg of oxalic acid, and 5 ml of 2N hydrochloric acid was refluxed by heating in an oil bath for 2 hours. The mixture was cooled and precipitated crystals were filtered. Then, 284 g of the crude crystals thus obtained were further recrystallized with 2N hydrochloric acid to give 201 mg of 6-cyano-7-(4-oxo-4H-pyridin-1-yl)-1,4-dihydroquinoxaline-2,3-dione.

Melting point: 410°–415° C. (decomposition) Elemental analysis (analyzed as $C_{14}H_8N_4O_3 \cdot \frac{3}{4}H_2O$) Calculated: C,57.23; H,3.26; N,19.07 (%) Found: C,57.54; H,3.33; N,19.10; (%) $H^1$-NMR ($D_2O$-$HNO_3$)δ: 7.50 (2H, d, J=8 Hz), 7.68 (1H, s), 7.88 (1H, s), 8.72 (2H, d, J=8 Hz).

EXAMPLE 8

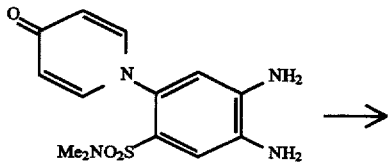

6-Dimethylsulfamoyl-7-(4-oxo-4H-pyridin-1-yl)-quinoxaline-2,3-dione

First, a mixture containing 500 mg of 4-dimethylsulfamoyl-5-(4-oxo-4H-pyridin-1-yl)-1,2-phenylenediamine, 438 mg of oxalic acid, and 10 ml of 2N hydrochloric acid was refluxed by heating in an oil bath for 3 hours. The mixture was cooled and made basic with aqueous ammonia. Precipitated crystals were filtered. Then, 534 mg of the crude crystals thus obtained were further recrystallized with dimethylformaldehyde and water to give 201 mg of 6-dimethylsulfamoyl-7-(4-oxo-4H-pyridin-1-yl)-1,4-dihydroquinoxaline-2,3-dione.

Melting point: 400°–405° C. (decomposition) Elemental analysis (analyzed as $C_{15}H_{14}N_4O_5S \cdot \frac{1}{4}H_2O$) Calculated: C,49.11; H,3.98; N,15.27; S,8.74 (%) Found: C,49.22; H,4.10; N,15.37; S,8.72 (%) $H^1$-NMR ($D_2O$-$HNO_3$)δ: 2.17 (6H, s), 6.91 (2H, d, J=7 Hz), 7.13 (1H, s), 7.37 (1H, s), 8.10 (2H, d, J=7 Hz).

EXAMPLE 9

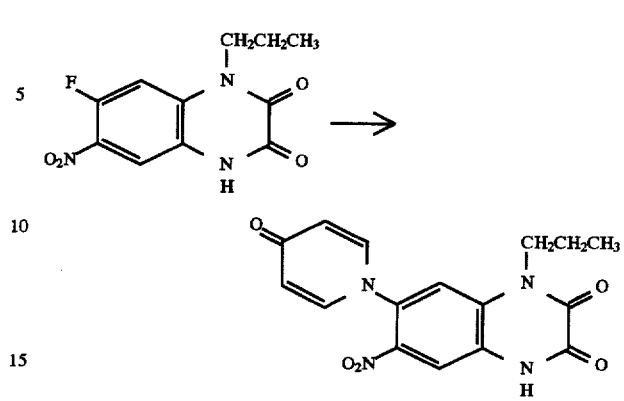

6-Nitro-7-(4-oxo-4H-pyridin-1-yl)-1-(n-propyl)-1,4-dihydroquinoxaline-2,3-dione

First, 1.244 g of 7-fluoro-6-nitro-1-(n-propyl)-1,4-dihydroquinoxaline-2,3-dione, 952 mg of 4-hydroxypyridine, and 711 mg of powdered potassium hydroxide were added to 10 ml of dry dimethylsulfoxide. The mixture was stirred at 130° C. for 3.5 hours in a nitrogen atmosphere. Then, 50 ml of water was added to the reaction mixture and the mixture was made acidic (pH 2 to 3) with 4N hydrochloric acid to give a yellow precipitate. The precipitate was filtered and recrystallized with dimethylformaldehyde to give 1.08 g of 6-nitro-7-(4-oxo-4H-pyridin-1-yl)-1-(n-propyl)-1,4-dihydroquinoxaline-2,3-dione.

Melting point: >300° C. Elemental analysis (analyzed as $C_{16}H_{14}N_4O_5 \cdot 0.2H_2O$) Calculated: C,55.56; H,4.20; N, 16.20 (%) Found: C,55.63; H,4.29; N, 16.37 (%) $H^1$-NMR ($d_6$-DMSO)δ: 0.94 (3H, t, J=7.2 Hz), 1.65 (2H, m), 4.10 (2H, m), 6.21 (2H, d, J=7.6 Hz), 7.77 (2H, d, J=7.6 Hz), 7.86 (1H, s), 8.02 (1H, s).

EXAMPLE 10

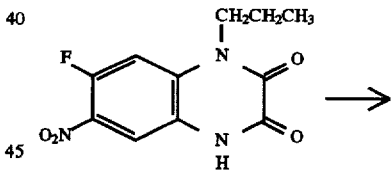

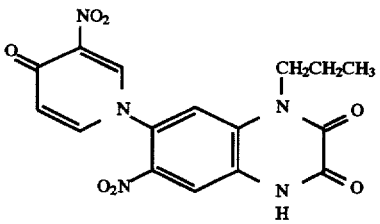

6-Nitro-7-(3-nitro-4-oxo-4H-pyridin-1-yl)-1-(n-propyl)-1,4-dihydroquinoxaline-2,3-dione First, 803 mg of 7-fluoro-6-nitro-1-(n-propyl)-1,4-dihydroquinoxaline-2,3-dione, 700 mg of 3-nitro-4-hydroxypyridine, and 365 mg of potassium hydroxide were allowed to react at 130° C. for 4.5 hours in dry dimethylsulfoxide in the same way as in Example 9 to give 1.059 g of 6-nitro-7-(3-nitro-4-oxo-4H-pyridin-1-yl)-1-(n-propyl)-1,4-dihydroquinoxaline-2,3-dione.

Melting point: >300° C. Elemental analysis (analyzed as $C_{16}H_{13}N_5O_7 \cdot 0.3H_2O$) Calculated: C,48.94; H,3.49; N,17.83

(%) Found: C,49.02; H,3.68; N,17.92 (%) H¹-NMR (d₆-DMSO)δ: 0.94 (3H, t, J=7.4 Hz), 1.66 (2H, m), 4.06 (2H, m), 6.64 (1H, d, J=7.8 Hz), 7.98 (1H, m), 8.00 (1H, s), 8.10 (1H, s), 9.12 (1H, d, J=1.8 Hz), 12.46(1H, br.s).

EXAMPLE 11

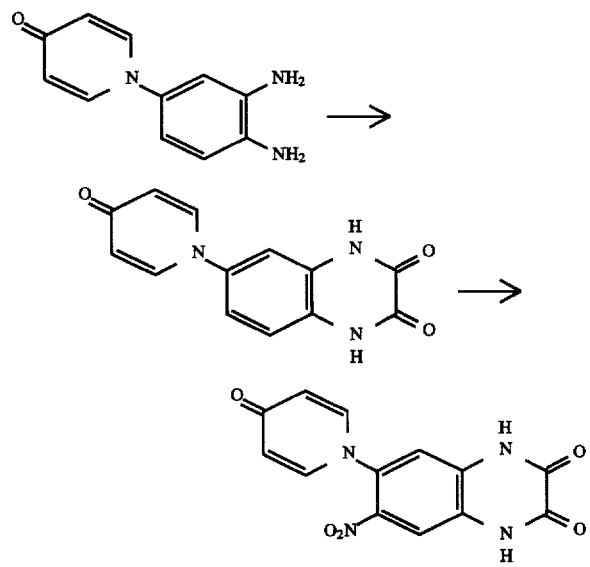

6-(4-Oxo-4H-pyridin-1-yl)-1,4-dihydroquinoxaline-2,3-dione

First, 4.849 g of 4-(4-oxo-4H-pyridin-1-yl)-1,2-phenylenediamine and 2.402 g of oxalic acid were added to 60 ml of 4N hydrochloric acid. The mixture was refluxed by heating for 2.5 hours in a nitrogen atmosphere. After the mixture was cooled, precipitated crystals were filtered and recrystallized with dimethylformamide to give 4.786 g of 6-(4-oxo-4H-pyridin-1-yl)-1,4-dihydroquinoxaline-2,3-dione.

Melting point: >300° C. Elemental analysis (analyzed as C₁₃H₉N₃O₃) Calculated: C,61.18; H,3.55; N,16.46 (%) Found: C,60.94; H,3.62; N,16.37 (%). 6-Nitro-7-(4-oxo-4H-pyridin-1-yl)-1,4-dihydroquinoxaline-2,3-dione First, 510 mg of 6-(4-oxo-4H-pyridin-1-yl)-1,4-dihydroquinoxaline-2,3-dione was added to 5 ml of conc. sulfuric acid with ice-cooling and dissolved therein. Then, 253 mg of potassium nitrate was added to the resultant solution. The mixture was heated at 60° C. for 3 hours with stirring. Then, 20 ml of ice water was added to the mixture and the pH of the solution was adjusted to 5 with a solution of 4N sodium hydroxide. The precipitated yellow crystals were filtered. The crystals thus obtained were washed with water and dried to give 426 mg of 6-nitro-7-(4-oxo-4H-pyridin-1-yl)-1,4-dihydroquinoxaline-2,3-dione.

Melting point: >300° C. H¹-NMR (d₆-DMSO)δ: 6.20 (2H, d, J=7.8 Hz), 7.20 (1H, s), 7.76 (2H, d, J=7.8 Hz), 7.99 (1H, s).

H¹-NMR and HPLC confirmed that the compound 6-nitro-7-(4-oxo-4H-pyridin-1-yl)-1,4-dihydroquinoxaline-2,3-dione was the same material as Compound Ia obtained in Example 1.

EXAMPLE 12

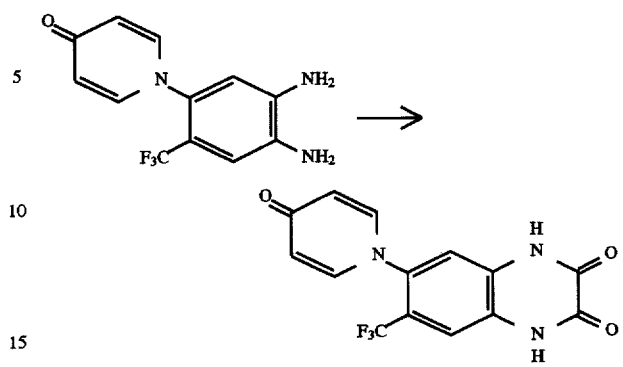

6-(4-Oxo-4H-pyridin-1-yl)-7-trifluoromethyl-1,4-dihydroquinoxaline-2,3-dione

First, a mixture containing 300 mg of 4-(4-oxo-4H-pyridin-1-yl)-5-trifluoromethyl-1,2-phenylenediamine, 301 mg of oxalic acid, and 6 ml of 2N hydrochloric acid was refluxed by heating in an oil bath for 7 hours. The mixture was cooled and precipitated crystals were filtered. Then, 333 mg of the crude crystals thus obtained were recrystallized with a mixture of dimethylformamide and water to give 216 mg of 6-(4-oxo-4H-pyridin-1-yl)-7-trifluoromethyl-1,4-dihydroquinoxaline-2,3-dione.

Melting point: 410°–420° C. Elemental analysis (analyzed as C₁₄H₈N₃O₃F₃.¼H₂O) Calculated: C,51.31; H,2.61; N,12.82; F,17.39 (%) Found: C,51.36; H,2.87; N,13.04; F,17.11 (%) H¹-NMR (d₆-DMSO)δ: 6.18 (2H, d, J=8 Hz), 7.22 (1H, s), 7.55 (1H, s), 7.70 (2H, d, J=8 Hz), 12.33 (2H, br)

EXAMPLE 13

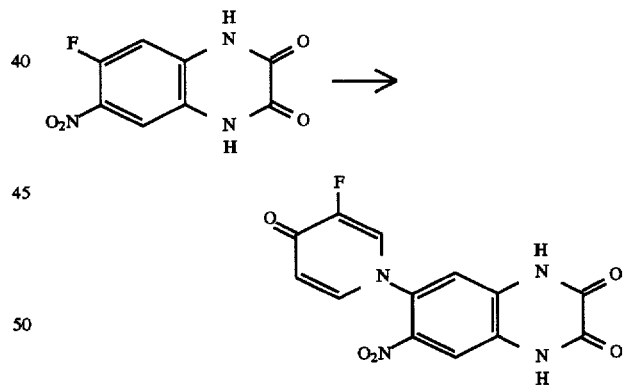

6-Nitro-7-(3-fluoro-4-oxo-4H-pyridin-1-yl)-1,4-dihydroquinoxaline-2,3-dione

First, 127 mg of 7-fluoro-6-nitro-1,4-dihydroquinoxaline-2,3-dione, 96 mg of 3-fluoro-4-hydroxypyridine, and 55 mg of powdered potassium hydroxide were added to 12 ml of dry dimethylsulfoxide. The mixture was stirred at 130° C. for 3 hours in a nitrogen atmosphere. Then, 50 ml of ice water was added to the reaction mixture, and the mixture was neutralized with 2N hydrochloric acid. The resultant precipitate was filtered and washed with water. The precipitate was dissolved in 3 ml of 1N sodium hydroxide. The solution was treated with activated carbon and filtered. The filtrate was neutralized with conc. hydrochloric acid. The precipitated crystals were filtered and dried to give 147 mg of 6-nitro-7-(3-fluoro-4-oxo-4H-pyridin-1-yl)-1,4-dihydroquinoxaline-2,3-dione.

Melting point: >300° C. Elemental analysis (analyzed as $C_{13}H_7N_4O_5F\cdot0.3H_2O$) Calculated: C,48.25; H,2.37; N,17.31; F,5.87 (%) Found: C,48.09; H,2.61; N,17.49; F,6.27 (%) $H^1$-NMR ($d_6$-DMSO)δ: 6.46 (1H, dd, J=9.0, 7.4 Hz), 7.28 (1H, s), 7.85 (1H, dd, J=7.6, 2.0 Hz), 8.08 (1H, s), 8.37 (1H, dd, J=7.8, 2.0 Hz).

EXPERIMENTAL EXAMPLE 1

Assay for competitive binding of 6-nitro-7-(4-oxo-4H-pyridin-1-yl)-1,4-dihydroquinoxaline-2,3-dione (Ia) to a glycine binding site of NMDA receptors.

First, the cerebral cortex of an Slc-Wistar rat (250 to 300 g in weight) was homogenized in 5 mM Tris acetic acid buffer in 20-fold volume (containing 1 mM EGTA, 0.1 mM PMSF, and 0.01% Bacitracin, pH 7.4). The cerebral cortex was centrifuged at 50,000×g for 30 minutes and resuspended in a buffer. This process was repeated four times. The final suspension was stored at −80° C. The frozen suspension was thawed at room temperature and incubated with 0.08% Triton X-100 solution at 2° C. for 10 minutes. The resultant suspension was then washed twice and suspended in 50 mM Tris-acetate buffer (pH 7.4) to give a membrane sample. The membrane sample was mixed with 100 nM [$^3$H]glycine and solutions in a series of concentrations of Compound Ia obtained in Example 1. The mixtures were incubated at 0° C. for 10 minutes. Each of the mixtures was diluted and filtered using Whatman GF/C filter paper so as to terminate the reaction, and radioactivity of $^3$H remaining on the filter paper was measured by a scintillation counter for liquid. The assay for non-specific binding was conducted with 1 mM of non-radioactive glycine to determine an $IC_{50}$ value. $IC_{50}$ value of Compound Ia was determined using YM900 (a compound of Example 15 described in WO92/07847) as a control in the same way as described above. The results are shown in Table 2.

TABLE 2

| Compound | $IC_{50}$ (μM)[a] |
|---|---|
| Ia | 6.6 |
| YM900 | 67 |

[a] [$^3$H] glycine was used.

Compound Ia exhibited antagonistic effects approximately ten times as strong as that of YM900.

EXPERIMENTAL EXAMPLE 2

Assay for competitive binding of 6-nitro-7-(4-oxo-4H-pyridin-1-yl)-1,4-dihydroquinoxaline-2,3-dione (Ia) to AMPA receptors.

First, the cerebral cortex of an Slc-Wistar rat (250 to 300 g in weight) was homogenized in 30 mM Tris acetic acid buffer in 10-fold volume (containing 2.5 mM $CaCl_2$, pH 7.1). The cerebral cortex was centrifuged at 30,000×g for 15 minutes and resuspended in a buffer. This process was repeated three times. The final suspension was stored at −80° C. The frozen suspension was thawed at room temperature and suspended in 30 mM Tris-acetate buffer (containing 2.5 mM $CaCl_2$ and 100 mM KSCN, pH 7.1) to give a membrane sample. The membrane sample was mixed with 30 nM [$^3$H]AMPA and solutions in a series of concentrations of Compound Ia. The mixtures were incubated at 0° C. for 30 minutes. Each of the mixtures was diluted and filtered using Whatman GF/C filter paper so as to terminate the reaction, and radioactivity of $^3$H remaining on the filter paper was measured by a scintillation counter for liquid. The assay for non-specific binding was conducted with 1 mM non-radioactive glutamate to determine an $IC_{50}$ value. $IC_{50}$ value of Compound Ia was determined using YM900 as a control in the same way as described above. The results are shown in Table 3.

TABLE 3

| Compound | $IC_{50}$(μM)[a] |
|---|---|
| Ia | 0.10 |
| YM900 | 0.28 |

[a] [$^3$H]AMPA was used.

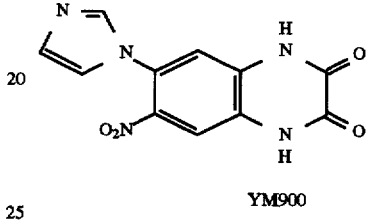

YM900

According to the present invention, oxopyridinylquinoxaline derivatives, which are novel compounds, exhibit outstanding antagonistic effects in connection with the NMDA receptors and the AMPA receptors of central neurons. The compounds of the present invention are effective as therapeutic agents for neurological disorders caused by excitatory amino acids since they inhibit the excitatory amino acids from binding to the NMDA receptors or the AMPA receptors.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. An oxopyridinylquinoxaline derivative represented by the following Formula I or pharmaceutically acceptable salts thereof:

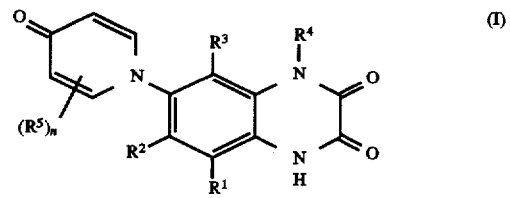

wherein $R^1$ is hydrogen, halogen, nitro, or trihalomethyl; $R^2$ is hydrogen, halogen, nitro, cyano, trihalomethyl, carbamoyl, carbamoyl substituted with lower alkyl, sulfamoyl, or sulfamoyl substituted with lower alkyl; $R^3$ is hydrogen, nitro, or halogen; $R^4$ is hydrogen, lower alkyl, substituted lower alkyl, lower cycloalkyl, or substituted lower cycloalkyl; $R^5$'s are substituents independently selected from the group consisting of halogen, nitro, cyano, lower alkyl, carbamoyl, and carbamoyl substituted with lower alkyl; and n is an integer of 0 to 4.

2. The oxopyridinylquinoxaline derivative or pharmaceutically acceptable salts thereof according to claim 1, wherein $R^1$ and $R^3$ are independently hydrogen or nitro; $R^2$ is halogen, nitro, cyano, trihalomethyl, carbamoyl, carbamoyl substituted with lower alkyl, sulfamoyl, or sulfamoyl substituted with lower alkyl; $R^4$ is hydrogen or lower alkyl; $R^5$'s are substituents independently selected from the group consisting of halogen, nitro, and lower alkyl; and n is an integer of 0 to 4.

3. The oxopyridinylquinoxaline derivative or pharmaceutically acceptable salts thereof according to claim 1, wherein each of $R^1$ and $R^3$ is hydrogen; $R^2$ is halogen, nitro, cyano, or trihalomethyl; $R^4$ is hydrogen or lower alkyl; $R^5$'s are substituents independently selected from the group consisting of halogen and nitro; and n is an integer of 0 to 4.

4. The oxopyridinylquinoxaline derivative according to claim 1, wherein n is 0.

5. The oxopyridinylquinoxaline derivative or pharmaceutically acceptable salts thereof according to claim 4, wherein each of $R^1$, $R^2$, and $R^4$ is hydrogen; and $R^2$ is nitro.

6. A method for treating a neurological disease caused by hyper-stimulation of neurons due to excitatory amino acids, comprising the step of administering to a subject, in vivo, a therapeutically effective amount of the compound of claim 1.

7. A method according to claim 6, wherein the compound has antagonistic activities for glutamate receptor.

8. A method according to claim 6, wherein the neurological disease is treated by competitively inhibiting the hyper-stimulation of neurons by excitatory amino acids.

9. A method according to claim 6, wherein the neurological disease is at least one selected from the group consisting of parkinsonism, senile dementia, Huntington's chorea and epilepsia.

10. A pharmaceutical composition comprising an oxopyridinylquinoxaline derivative represented by the following Formula I or pharmaceutically acceptable salts thereof as its active component:

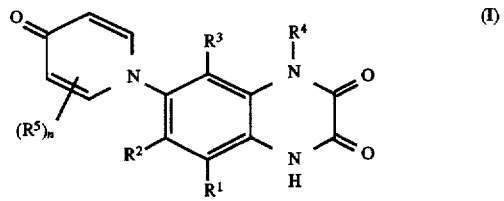

(I)

wherein $R^1$ is hydrogen, halogen, nitro, or trihalomethyl; $R^2$ is hydrogen, halogen, nitro, cyano, trihalomethyl, carbamoyl, carbamoyl substituted with lower alkyl, sulfamoyl, or sulfamoyl substituted with lower alkyl; $R^3$ is hydrogen, nitro, or halogen; $R^4$ is hydrogen, lower alkyl, substituted lower alkyl, lower cycloalkyl, or substituted lower cycloalkyl; $R^5$'s are substituents independently selected from the group consisting of halogen, nitro, cyano, lower alkyl, carbamoyl, and carbamoyl substituted with lower alkyl; and n is an integer of 0 to 4.

* * * * *

UNITED STATES PATENT AND TRADEMARK OFFICE
CERTIFICATE OF CORRECTION

PATENT NO. : 5,677,305
DATED : October 14, 1997
INVENTOR(S) : Takada, Chomei, Adachi, Eigyo, and Kawasaki It is certified that error appears in the above-identified patent and that said Letters Patent is hereby corrected as shown below:

At column 25, claim 5, the first --$R^2$-- should read $R^3$.

Signed and Sealed this

Twenty-fourth Day of March, 1998

Attest:

BRUCE LEHMAN

*Attesting Officer*   *Commissioner of Patents and Trademarks*